United States Patent
Qian et al.

(10) Patent No.: US 10,088,992 B2
(45) Date of Patent: Oct. 2, 2018

(54) ENABLING A USER TO STUDY IMAGE DATA

(71) Applicants: KONINKLIJKE PHILIPS N.V., Eindhoven (NL); PHILIPS MEDICAL SYSTEMS TECHNOLOGIES LTD, Haifa (IL)

(72) Inventors: Yuechen Qian, Briarcliff Manor, NY (US); Eran Rubens, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 401 days.

(21) Appl. No.: 14/782,350

(22) PCT Filed: Apr. 11, 2014

(86) PCT No.: PCT/IB2014/060646
§ 371 (c)(1),
(2) Date: Oct. 5, 2015

(87) PCT Pub. No.: WO2014/167536
PCT Pub. Date: Oct. 16, 2014

(65) Prior Publication Data
US 2016/0041733 A1 Feb. 11, 2016

Related U.S. Application Data

(60) Provisional application No. 61/810,752, filed on Apr. 11, 2013.

(51) Int. Cl.
*G06F 3/048* (2013.01)
*G06F 3/0484* (2013.01)
(Continued)

(52) U.S. Cl.
CPC ........ *G06F 3/04845* (2013.01); *G06F 3/0482* (2013.01); *G06F 19/321* (2013.01);
(Continued)

(58) Field of Classification Search
None
See application file for complete search history.

(56) References Cited

U.S. PATENT DOCUMENTS

2009/0037840 A1  2/2009  Chen
2009/0178004 A1*  7/2009  Stoval, III  ............ G06F 19/322
715/812

(Continued)

FOREIGN PATENT DOCUMENTS

WO  2007020598 A2  2/2007
WO  2007050962 A2  5/2007
WO  2012052887 A2  4/2012

*Primary Examiner* — Claudia Dragoescu

(57) ABSTRACT

A system (100) for enabling study of image data, comprising: —a user interface subsystem (120) for i) receiving navigation commands (022) from a user, and ii) displaying different views (400) of the image data (042) in response to the navigation commands for enabling the user to navigate through the image data; —a function execution subsystem (160) for executing individual ones of a plurality of system functions (500) to support the user in the study of the image data; and—a pattern analysis subsystem (140) for: j) obtaining, from the user interface subsystem, data (022) indicative of a display sequence of the different views during the navigating through the image data, jj) analyzing the data to determine a navigation pattern (631) of the user, and jjj) based on the navigation pattern, selecting one of the plurality of system functions for execution by the function execution subsystem.

15 Claims, 4 Drawing Sheets

(51) Int. Cl.
  *G06F 19/00* (2018.01)
  *G06F 3/0482* (2013.01)
  *G06T 7/00* (2017.01)
  *G06T 7/174* (2017.01)
  *G16H 50/70* (2018.01)
  *G16H 50/20* (2018.01)

(52) U.S. Cl.
  CPC ............ *G06T 7/0012* (2013.01); *G06T 7/174* (2017.01); *G16H 50/20* (2018.01); *G16H 50/70* (2018.01); *G06T 2207/20112* (2013.01)

(56) References Cited

U.S. PATENT DOCUMENTS

| | | |
|---|---|---|
| 2012/0123801 A1 | 5/2012 | Opfer et al. |
| 2012/0131498 A1 | 5/2012 | Gross et al. |
| 2012/0172700 A1* | 7/2012 | Krishnan ............... A61B 6/032 600/407 |

* cited by examiner

ENABLING A USER TO STUDY IMAGE DATA

CROSS-REFERENCE TO PRIOR APPLICATIONS

This application is the U.S. National Phase application under 35 U.S.C. § 371 of International Application No. PCT/IB2014/060646, filed on Apr. 11, 2014, which claims the benefit of U.S. Provisional Application No. 61/810,752, filed on Apr. 11, 2013. These applications are hereby incorporated by reference herein.

FIELD OF THE INVENTION

The invention relates to a system and a method for enabling study of image data. The invention further relates to a workstation and imaging apparatus comprising the system and to a computer program product for performing the method.

BACKGROUND OF THE INVENTION

In the field of image analysis and display, it is common to display different views of image data to enable a user to study the image data. For example, in medical imaging, Computed Tomography (CT), magnetic resonance imaging (MRI) or other modalities may provide three-dimensional (3D) image data of an anatomical structure. To enable a radiologist to study the anatomical structure, the 3D image data may be displayed to the radiologist as a sequence of different two-dimensional (2D) cross-sectional views of the anatomical structure. The radiologist may determine which 2D cross-sectional views are displayed by providing appropriate navigation commands.

A system providing the above functionality may also provide system functions which further support a user such as the radiologist in the study of the image data. For example, the system may provide system functions such as image annotation functions, image measurement functions, image analysis functions, image processing functions and reporting functions. Such functions may be selectable by the user, e.g., by clicking a corresponding icon onscreen. In response, the system may execute the selected system function, thereby, e.g., adding an annotation to a region of interest in the image data.

It is known to capture user actions which are performed on an image displaying device. WO 2007/050962 A2 describes an electronic image workflow method and system which includes a client workstation with a high-resolution image displaying device and an input device that captures actions that are performed on the image displaying device. It is said workflow templates may be created using various parameters that define the multi-media display and sequence of actions that are presented to users. Such workflow templates then provide end-users with the ability to follow a pre-designed workflow sequence. It is further said that computerized intelligence agents may also query, retrieve, and/or add additional data to the workflow templates in order to supplement data that is entered to the electronic medical record (EMR) by end-users. Such computerized intelligent agents may also learn to perform the user actions, including repetitive actions or other types of actions based on anatomy, clinical indications, patient profile, and/or other criteria.

A problem of the above electronic image workflow method and system is that it is insufficiently suitable for enabling a user to study image data in a convenient manner.

SUMMARY OF THE INVENTION

It would be advantageous to have a system or method for enabling a user to study image data in a more convenient manner.

To better address this concern, a first aspect of the invention provides a system for enabling study of image data, comprising:
  a user interface subsystem for i) receiving navigation commands from a user, and ii) displaying different views of the image data in response to the navigation commands for enabling the user to navigate through the image data;
  a function execution subsystem for executing individual ones of a plurality of system functions to support the user in the study of the image data; and
  a pattern analysis subsystem for:
    j) obtaining, from the user interface subsystem, data indicative of a display sequence of the different views during the navigating through the image data,
    jj) analyzing the data to determine a navigation pattern of the user, and
    jjj) based on the navigation pattern, selecting one of the plurality of system functions for execution by the function execution subsystem.

In a further aspect of the invention, a workstation and imaging apparatus is provided comprising the system set forth.

In a further aspect of the invention, a method is provided for enabling study of image data, comprising:
  receiving navigation commands from a user;
  displaying different views of the image data in response to the navigation commands for enabling the user to navigate through the image data; and
  executing individual ones of a plurality of system functions to support the user in the study of the image data;
  the method further comprising:
  obtaining data indicative of a display sequence of the different views during the navigating through the image data;
  analyzing the data to determine a navigation pattern of the user;
  based on the navigation pattern, selecting one of the plurality of system functions for said executing.

In a further aspect of the invention, a computer program product is provided comprising instructions for causing a processor system to perform the method set forth.

The above system and method enable a user to study image data in the following manner. A user interface subsystem is provided for displaying different views of the image data in response to navigation commands received from the user. The different views show different parts and/or perspectives of the image data. By providing appropriate navigation commands to the system, the user can navigate through the image data, i.e., obtain display of said different parts and/or perspectives of the image data. For example, in case the image data is volumetric image data, the system may calculate different views of the volumetric image data using techniques such as multi-planar reformatting (MPR) to enable the user to freely navigate through the volumetric image data. Another example is that when the image data is constituted by a stack of image slices, the system may display different images slices in response to forward and/or backward navigation commands, thereby enabling the user to scroll forward and/or backward through the stack of image slices.

A function execution subsystem is provided which is capable of executing a plurality of system functions to support the user in the study of the image data. The system functions support the user in that they, upon execution by the function execution subsystem, invoke one or more actions of the system which help the user in the study of the image data. Thus, the system performs one or more actions as part of executing such a system function.

Furthermore, a pattern analysis subsystem is provided for obtaining data from the user interface subsystem which is indicative of a display sequence of the different views during the navigating through the image data by the user. The data therefore enables the pattern analysis subsystem to determine which views are displayed and in which order. For example, the pattern analysis subsystem may obtain the data in the form of the navigation commands which allows determining which views are displayed and in which order. Another non-limiting example is that the pattern analysis subsystem may directly obtain a time-ordered list of displayed views from the user interface subsystem. The pattern analysis subsystem analyzes the data to determine whether, and if so, which navigation pattern exists when the user navigates through the image data. Here, the term navigation pattern refers to a structure in the user's navigation behavior. Having determined the navigation pattern, the pattern analysis subsystem selects one of the plurality of system functions based on the navigation pattern. Hence, the navigation pattern determines which one of the plurality of system function is selected. For that purpose, the pattern analysis subsystem may make use of pre-defined rules, a reasoning engine or any other suitable technique linking a specific navigation pattern to a specific system function. In response, the function execution subsystem may directly execute said selected system function, suggest the selected system function to the user for execution, etc. For example, the user interface subsystem may visually indicate the selected system function to the user, with the function execution subsystem only executing the selected system function after a request from the user.

The present invention is based in part on the recognition that a structure in the user's navigation behavior is indicative of the user's next steps in studying the image data, and in particular, is indicative of which system function or type of system function the user intends to request. For example, when the user repeatedly scrolls through a small subset of views, e.g., in a zigzag manner, this may indicate that the user intends to further analyze an object comprised in the small subset of views. Accordingly, the user may intend to request a system function relating to image analysis. The present invention has the effect that the system automatically selects the system function for execution based on the navigation pattern of the user. The system is enabled to determine the navigation pattern of the user since data is available to the system which enables the system to determine which views are displayed during navigation and in which order. As such, the system can determine whether a structure exists in the user's navigation behavior, i.e., the navigation pattern. Based on this navigation behavior, the system selects an appropriate system function for execution.

Accordingly, the user is automatically supported in the study of the image data in that the user does not need to manually select the system function. Advantageously, it is more convenient for the user to study the image data.

Advantageously, the user is not distracted from the study of the image data by having to manually select the system function.

Optionally, the pattern analysis subsystem is arranged for, after selecting the one of the plurality of system functions, i) instructing the function execution subsystem to execute said system function, or ii) instructing the user interface subsystem to visually indicate the system function to the user for enabling the user to request the execution of the system function. The system may thus directly execute the selected system function, or rather first suggest the system function to the user before executing the system function on request of the user. For example, in the latter case, the user interface subsystem may establish the selected system function as default selection, e.g., in a toolbar or menu, position a graphical representation of said system function next to the cursor for easy selection, etc.

Optionally, the pattern analysis subsystem is arranged for using mapping data to select the one of the plurality of system functions based on the navigation pattern, the mapping data being indicative of an association between the navigation pattern and the one of the plurality of system functions. The pattern analysis subsystem thus makes use of mapping data which suggests a link between the navigation pattern and the one of the plurality of system functions, thereby enabling the pattern analysis subsystem to select said system function. For example, the mapping data may be constituted by a look-up table which links a particular navigation pattern to a particular system function. Advantageously, the mapping data may be pre-computed, thereby allowing information to be taken into account which may otherwise be unavailable at a time of selection.

Optionally, the user interface subsystem is arranged for enabling the user to request execution of the individual ones of the plurality of system functions, and the mapping data is constituted by a history of requests and associated navigation patterns of the user. The user is thus enabled to manually select, i.e., request, individual ones of the plurality of system functions for execution. The pattern analysis subsystem uses a history of such requests and associated navigation patterns, i.e., navigation patterns at a time of making said requests, in the selection of the one of the plurality of system functions. The history of requests and associated navigation patterns enables the pattern analysis subsystem to correlate the past requests of the user with the past navigation patterns of the user, which in turn enables the pattern analysis subsystem to estimate an intended request of the user based on a current navigation pattern of the user. Advantageously, the automatic selection of the system function better matches an intention of the user.

Optionally, the pattern analysis subsystem is arranged for applying machine learning to the history of requests and associated navigation patterns of the user for enabling selecting the one of the plurality of system functions based on a presumed request of the user. Machine learning is well suited for correlating the past requests of the user with the past navigation patterns of user so as to enable better estimating the intended request of the user based on the current navigation pattern of the user.

Optionally, the pattern analysis subsystem is arranged for determining the navigation pattern by, based on the data, determining a display parameter for each of the different views, each of said display parameters characterizing the display of a respective one of the different views during the navigation; and analyzing said display parameters to determine the navigation pattern. The pattern analysis subsystem thus determines the navigation behavior of the user by firstly determining a display parameter for each the displayed views during the navigation, and then analyzing the display parameters. Each display parameter characterizes the display of the respective one of the different views during navigation in that it describes a particular aspect of the displaying the respective view during the navigation, such as, e.g., how long or how often each view is displayed. It has been found that such display parameters are well suited for characterizing the navigation behavior of the user during the navigating through the image data.

Optionally, the display parameter is one of the group of: a display duration, a display frequency, a navigation speed at a time of display, and a navigation direction at a time of display. Here, the term 'display duration' refers to a measure how long the respective view is displayed during the navigation, e.g., in relative or absolute terms; the term 'display frequency' refers to a measure how often, the respective view is displayed during the navigation; the term 'navigation speed' refers to the speed of navigating at the time of displaying the respective view; and the term 'navigation direction' refers to a direction of the navigating at the time of displaying the respective view. The above display parameters have been found to be well suited for characterizing the navigation behavior of the user during the navigating through the image data.

Optionally, the navigation pattern is one of the group of: a stationary navigation pattern, a continuous navigation pattern with a navigation speed below a speed threshold, a continuous navigation pattern with a navigation speed above the speed threshold and a zigzag navigation pattern. Here, the term 'stationary navigation pattern' refers to a pattern in which the user predominantly or exclusively views one or a small number of views, the term 'continuous navigation pattern' refers to a pattern in which the user continuously navigates through different views with a navigation speed being either above or below a speed threshold, and the term 'zigzag navigation pattern' refers to a pattern in which the user navigates back and forth through a small to medium number of views. The above navigation patterns have been found to be particularly indicative of the user's next steps in studying the image data and thus of the user's intended request.

Optionally, the pattern analysis subsystem is arranged for i) obtaining contextual information of the study of the image data, and ii) selecting the one of the plurality of system functions further based on the contextual information. Hence, the navigation pattern and the contextual information together determine which one of the plurality of system function is selected. This aspect of the present invention is based on the insight that contextual information of the study of the image data may be used to further improve the selection. For example, if several different system functions are deemed suitable for execution based on a current navigation pattern, the contextual information may be used to select between said system functions. Advantageously, the automatic selection of the system function better matches the intended request of the user.

Optionally, the pattern analysis subsystem is arranged for obtaining the contextual information from at least one of the group of: metadata of the image data, workflow information indicating a current phase of the study and study information indicating a reason for the study. The above contextual information has been found to be well suited for improving the selection of the system function. For example, metadata such as DICOM attributes of medical image data may be used to select a system function which is relevant for the type of medical image data. Another example is that workflow information may indicate whether the study is in a pre-reading phase, an interpretation phase or a reporting phase, thereby enabling selecting a system function which is relevant for the current phase of the study. Another example is that the reason for the study may indicate which types of system functions are relevant in the study of the image data.

Optionally, the system further comprises an image analysis subsystem for analyzing a content of the image data for establishing the contextual information of the study of the image data. The content of the image data is well suited for providing a context for the study of the image data since the content is typically the subject of the study. By providing an image analysis subsystem, the system is enabled to analyze the content of the image data and use the result to better select the system function.

Optionally, the image data is medical image data, and the image analysis subsystem is arranged for analyzing the content of the medical image data based on segmenting an anatomical structure and/or lesion in the medical image data.

Optionally, the plurality of system functions comprises at least one of the group of: an image annotation function, an image measurement function, an image analysis function, an image processing function, and a reporting function.

Optionally, the user interface subsystem is arranged for displaying a navigational aid based on the display parameters for enabling the user to navigate to frequently viewed views. The user interface subsystem thus uses the plurality of display parameters to display a navigational aid to the user which indicates to the user how to navigate to the frequently viewed views. For example, the user interface subsystem may display the navigational aid in the form of a graphical representation of a position of a current view in the image data with respect to the position of frequently viewed views. Advantageously, the user can easily navigate back to frequently viewed views, thereby further increasing the convenience for the user when studying the image data.

It will be appreciated by those skilled in the art that two or more of the above-mentioned embodiments, implementations, and/or aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
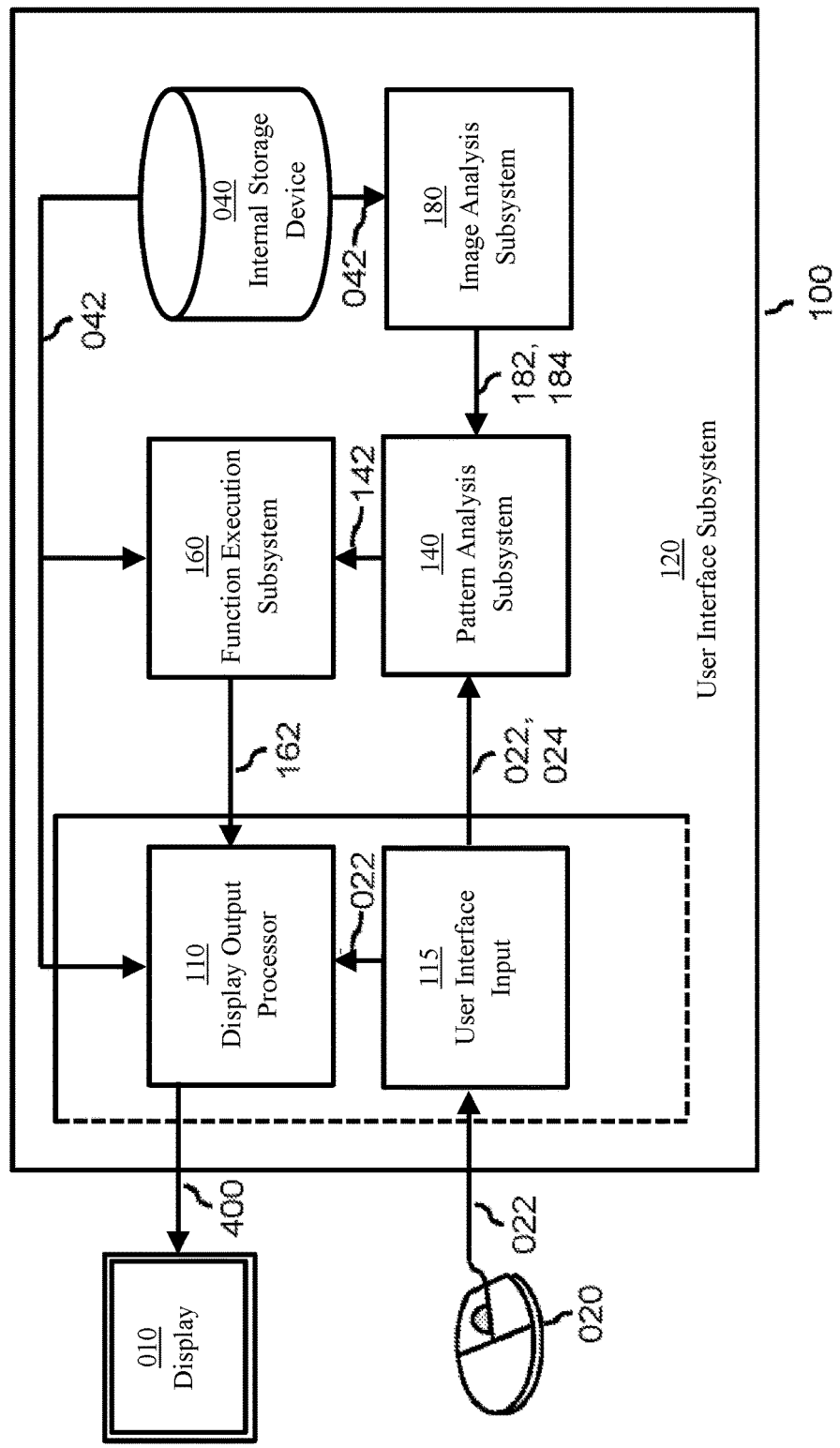
FIG. 1 shows a system for enabling a user to study image data.

FIG. 1 shows a system 100 for enabling a user to study image data. The system 100 comprises a user interface subsystem 120 for receiving navigation commands 022 from a user. For that purpose, the user interface subsystem 120 is shown to comprise a user interface input 115 which is connected to a user input device 020 such as a computer mouse. The user interface subsystem 120 is further shown to comprise a display output processor 110 for displaying different views 400 of the image data 042 in response to the navigation commands 022 so as to enable the user to navigate through the image data 042. For that purpose, the display output processor 110 is shown to receive the navigation commands 022 from the user interface input 115 and the image data 042 from an internal storage device 040. It is noted that instead of being received from the internal storage device 040, the image data 042 may also be received from an external storage device outside of the system 100. Moreover, the display output processor 110 is shown to provide the different views 400 to a display 010.

The system 100 further comprises a function execution subsystem 160 for executing individual ones of a plurality of system functions 500 to support the user in the study of the image data. To enable display of output 162 of the system functions, the function execution subsystem 160 is shown to be connected to the display output processor 110.

The system 100 further comprises a pattern analysis subsystem 140 for obtaining data from the user interface subsystem 120 which is indicative of a display sequence of the different views during the navigating through the image data. In the system 100 shown in FIG. 1, the data is obtained in the form of the navigation commands 022 which are indicative of which views are displayed and in which order. It will be appreciated, however, that the data may also take any other suitable form. For example, the pattern analysis subsystem 140 may also obtain a time-ordered list of displayed views from the user interface subsystem 120. Any future reference to the analysis of the navigation commands is therefore to be understood as a non-limiting example of the analysis of the earlier mentioned data. The pattern analysis subsystem 140 is arranged for analyzing the data, i.e., the navigation commands 022, to determine a navigation pattern of the user when navigating through the image data 042. The pattern analysis subsystem 140 is further arranged for, based on the navigation pattern, selecting one of the plurality of system functions for execution by the function execution subsystem 160. For that purpose, the pattern analysis subsystem 140 is shown to provide selection data 142 to the function execution subsystem 160 which may cause the function execution subsystem 160 to execute the system function.

An operation of the system 100 may be briefly explained as follows. The user interface subsystem 120 receives navigation commands 022 from the user. In response, the user interface subsystem 120 displays different views 400 of the image data 042. As such, the user is enabled to navigate through the image data 042. Simultaneously or subsequently, the pattern analysis subsystem 140 analyzes the data, e.g., the navigation commands 022, to determine a navigation pattern of the user when navigating through the image data 042. Based on the navigation pattern, the pattern analysis subsystem 140 selects one of the plurality of system functions 500 for execution. In response, the function execution subsystem 160 may directly execute the selected one of the plurality of system functions 500. Alternatively, the function execution subsystem 160 may first suggest the execution of the system function to the user, e.g., via an onscreen message, an increased prominence of a onscreen representation of the system function, etc, and only execute the system function after receiving confirmation from the user.

Figure 2:
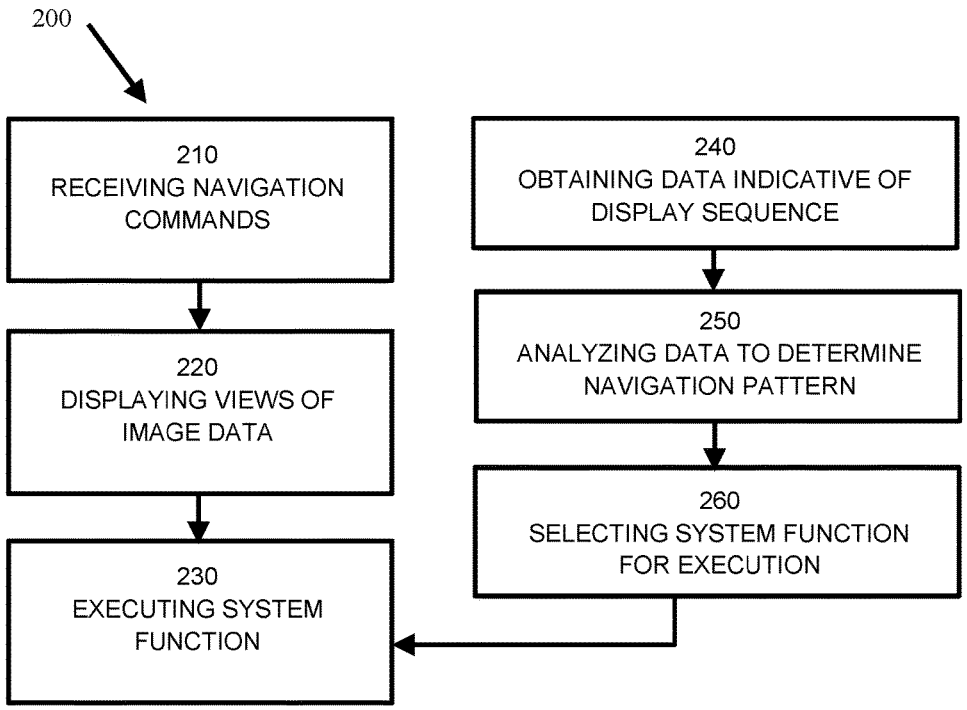
FIG. 2 shows a method for enabling a user to study image data.

FIG. 2 shows a method 200 for enabling a user to study image data. The method 200 may correspond to an operation of the system 100. However, the method 200 may also be performed in separation of the system 100, e.g., using a different system or device. The method 200 comprises, in a step titled "RECEIVING NAVIGATION COMMANDS", receiving 210 navigation commands from a user. The method 200 further comprises, in a step titled "DISPLAYING VIEWS OF IMAGE DATA", displaying 220 different views of the image data in response to the navigation commands for enabling the user to navigate through the image data. The method 200 further comprises, in a step titled "EXECUTING SYSTEM FUNCTION", executing 230 individual ones of a plurality of system functions to support the user in the study of the image data. The method 200 further comprises, in a step titled "OBTAINING DATA INDICATIVE OF DISPLAY SEQUENCE", obtaining 240 data indicative of a display sequence of the different views during the navigating through the image data. The method 200 further comprises, in a step titled "ANALYZING DATA TO DETERMINE NAVIGATION PATTERN", analyzing 250 the data to determine a navigation pattern of the user. The method 200 further comprises, in a step titled "SELECTING SYSTEM FUNCTION FOR EXECUTION", based on the navigation pattern, selecting 260 one of the plurality of system functions for executing 230.

It will be appreciated that the steps of obtaining 240, analyzing 250 and selecting 260 may be performed simultaneously with the steps of receiving 210 and displaying 220. Alternatively, the steps of obtaining 240, analyzing 250 and selecting 260 may be performed after performing the steps of receiving 210 and displaying 220. It is noted that, in general, the above steps may also be performed in any other suitable order.

Figure 3:
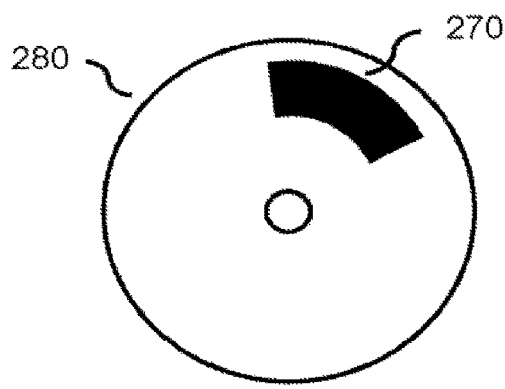
FIG. 3 shows a computer program product for performing the method.

FIG. 3 shows a computer program product 270 comprising instructions for causing a processor system to perform the aforementioned method 200. The computer program product 270 may be comprised on a computer readable medium 280, for example in the form of as a series of machine readable physical marks and/or as a series of elements having different electrical, e.g., magnetic, or optical properties or values.

The system 100 and the method 200 may be explained in more detail as follows. Here, continued reference is made to the FIG. 1, as well as to FIGS. 4-6d.

Figure 4:
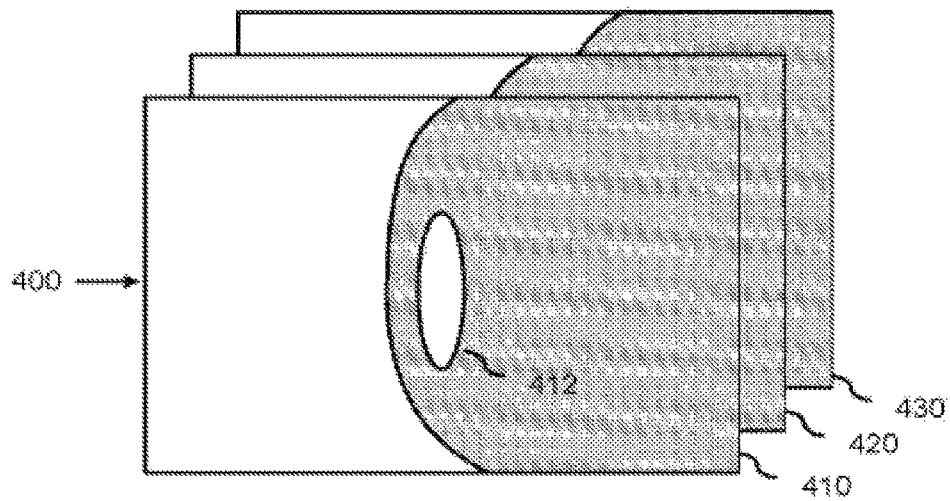
FIG. 4 illustratively shows different views of the image data.

FIG. 4 illustratively shows different views 400 which are displayed while the user navigates through the image data 042. Here, a first one 410 of the different views 400, i.e., a first view 410, is shown as an image on top of a stack of images that forms a representation of a part of the image data 042. FIG. 4 also partially shows a second 220 and third 230 one of the different views 400, i.e., a second view 420 and a third view 430, behind the first view 410. The system 100 may not actually display the different views 400 in the form of the aforementioned stack. For example, it may be desirable to only show a single view at a time, i.e., a current view 410. This may allow the user to focus on the particular view. Moreover, other forms of display are equally possible. Also the number of different views 400 may vary. For example, if the image data 042 is constituted by a stack of image slices, the number of different views 400 of the image data 042 may correspond to the number of image slices in the stack. This is not a limitation, however, in that the number of different views 400 may also be larger than the number of image slices, e.g., if multi-planar reformatting is used to generate oblique views of the stack of image slices.

Figure 5:
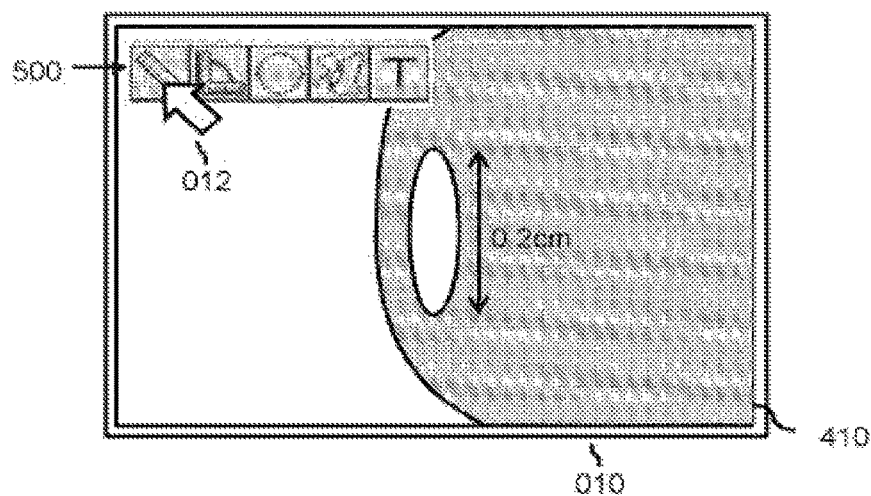
FIG. 5 shows the user manually selecting a system function for execution, and an output of the system function being displayed in a current view of the image data.

FIG. 4 shows the first view 410 being displayed to the user on the display 010. The first view 410, henceforth referred to also as current view 410, is shown to comprise an object 412. The object 412 may be of interest to the user, i.e., constitute an object or region of interest. Accordingly, the object 412 may be relevant in the study of the image data 042. FIG. 5 shows a toolbar comprising icons representing a plurality of system functions 500 which are provided by the system 100 for execution. The plurality of system functions 500 are shown to comprise several image measurement functions and image annotation functions. This is not a limitation, however, in that the plurality of system functions 500 may equally be comprised of one or more image analysis functions, image processing functions, reporting functions or other system functions that are suitable for supporting the user in the study of the image data 042. In the example of FIG. 5, the user interface subsystem 120 is arranged for enabling the user to request execution of individual ones of the plurality of system functions 500, e.g., by clicking with a cursor 012 on a respective one of the icons of the toolbar. FIG. 5 further shows a result of the user selecting an image measurement function, and in particular of the user selecting a distance measurement function as represented by an icon comprising a ruler. As a result, the user may be provided with an on-screen measurement tool for measuring a distance, e. g., the height of the object 412. The output of the distance measurement function may be displayed by the system 100 together or as part of the first view 410, e.g., in the form of the measured distance of "0.2 cm" being displayed.

The present invention enables system functions such as those of the above type, i.e., those being manually selectable by the user, to be automatically selected for execution by the system 100. It is noted, however, that the present invention is not limited to the selection of system functions which are also manually selectable by the user. Rather, one or more system functions may not be available for manual selection.

Figure 6A:
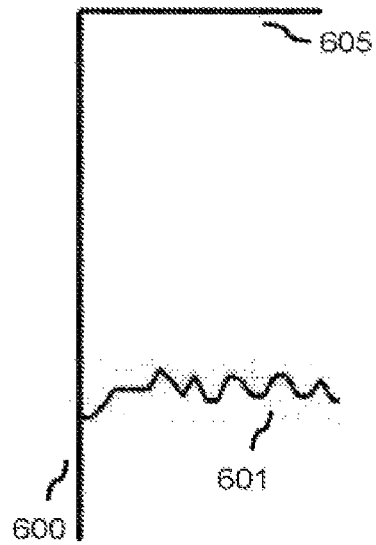
FIG. 6a schematically shows which of the different views are viewed by the user and in which order, as determined by the system based on navigation commands.

To enable automatically selecting one of the plurality of system functions 500 for execution by the function execution subsystem 160, the pattern analysis subsystem 140 analyzes the navigation commands 022 to determine a navigation pattern of the user when navigating through the image data 042. FIG. 6a schematically shows an example of a first step of the analysis, in that the pattern analysis subsystem 140 may determine which of the different views 400 are viewed by the user and in which order. Accordingly, the pattern analysis subsystem 140 may determine how the user navigates through the image data 042, i.e., which views are displayed and in which order. In FIG. 6a, the horizontal axis 605 corresponds to time and the vertical axis 600 corresponds to the view index. The line 601 thus indicates which views are viewed as a function of the time. It can be seen that the user initially continuously scrolls through the different views 400, and subsequently repetitively scrolls back and forth through several of the different views 400. In this respect, it is noted that the term 'scrolling' is to be understood as referring to a form of navigating which is typically, but not necessarily, performed using a scroll wheel of a computer mouse.

Figure 6B:
FIG. 6b shows a display frequency of each of the different views.

In order to determine the navigation pattern, the pattern analysis subsystem 140 may first determining a display parameter for each of the different views 400, each of said display parameters characterizing the display of a respective one of the different views during the navigation. FIG. 6b shows an example of a display parameter in the form of a display frequency 611 of each of the different views. Here, the vertical axis 610 corresponds to the view index whereas the horizontal axis 615 corresponds to a display frequency of each of the different views, i.e., indicate how often each view is displayed. It is noted that the display frequency 611 in the example of FIG. 6b was determined over a longer navigation period than was used in FIG. 6a, i.e., both Figures shows different parts of the navigation. From FIG. 6b, it can be seen that a select number of views are frequently displayed during navigation whereas other views are less frequently displayed or not at all.

Figure 6C:
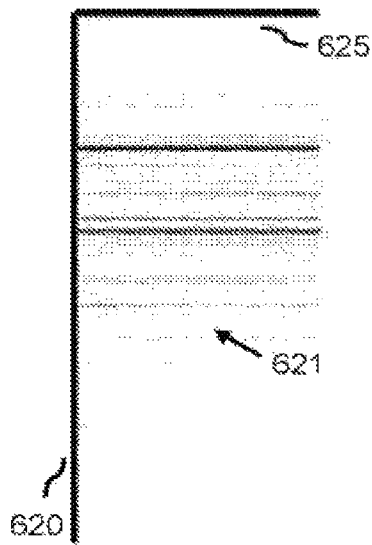
FIG. 6c shows an accumulated display time of each of the different views.

FIG. 6c shows another example of a display parameter in the form of an accumulated display time 621 of each of the different views. Here, the vertical axis 620 corresponds to the view index, whereas the horizontal axis 625 corresponds to the accumulated display time 621 of each of the different views, i.e., how long each of the different views is displayed in total during the navigation. The accumulated display time 621 is displayed in the form of gray-scale coding of the bars, with a darker gray indicating a longer display time and a lighter gray indicating a shorter display time. From FIG. 6c, it can be seen that a select number of views are displayed for a prolonged time during navigation whereas other views are only displayed for a short time or not displayed at all.

Although not shown in the previous Figures, the pattern analysis subsystem 140 may additionally or alternatively determine display parameters such as a navigation speed at a time of display, a navigation direction at a time of display, etc.

Figure 6D:
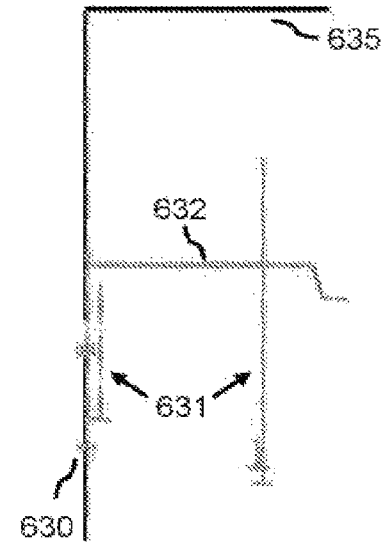
FIG. 6d shows zigzag navigation patterns as determined by the system.

The pattern analysis subsystem 140 may be arranged for analyzing the display parameters 611, 621 to determine the navigation pattern. Examples of such navigation patterns include a stationary navigation pattern, a continuous navigation pattern with a navigation speed below a speed threshold, a continuous navigation pattern with a navigation speed above the speed threshold and a zigzag navigation pattern. An example of the latter being detected by the system 100 is shown in FIG. 6d. Here, the horizontal axis 635 corresponds to time and the vertical axis corresponds to the view index 630. FIG. 6d further shows zigzag navigation patterns 631 being determined, with the zigzag navigation patterns 631 each being indicated by a vertical line bounded by a short horizontal line indicating a reversing of the navigation direction, i.e., a zigzag. It can be seen that, when reading FIG. 6d from right to left, the user first navigates through a broad range of different views, as indicated by the long vertical line. Subsequently, the user pauses navigation over a prolonged period. Only after that, the user navigates repeatedly back and forth through a narrower range, as indicated in FIG. 6d by the closely adjacent vertical lines near the vertical axis 630.

In general, a stationary navigation pattern may be determined based on one or a small number of adjacent views having a long display time. A continuous navigation pattern may be determined based on the user navigating substantially linearly through a series of views, i.e., without substantial changes in navigation direction and with each of the views having a similar display time. A zigzag navigation pattern may be determined based on the user navigating back and forth through a small to medium number of views. An example of the latter is the following. Here, as data from the user interface subsystem 120, a time-ordered list of displayed views is obtained, each line showing <time, view#>:

<1, 0>
<2, 0>
<3, 0>
<4, 1>
<5, 2>
<6, 4>
<7, 6>
<8, 9>
<9, 9>
<10, 9>
<11, 10>
<12, 11>
<13, 14>
<14, 14>
<15, 9>
<16, 14>

Given the above navigation commands 022, the pattern analysis subsystem 140 may determine that the total amount viewing time of view 0 is 3 and that of view 9 is 4. Moreover, the relative display duration of view 0 is 3/16 and that of view 9 is 4/16. In terms of display frequency, view 9 is displayed during two separate visits whereas the rest of views are only displayed during one visit. In order to determine the presence of a zigzag navigation pattern, the pattern analysis subsystem 140 may compute the navigation speed at each of the timestamps. For example, at timestamp 13, the navigation speed is 3 views per timestamp; at timestamp 14, the speed is 0; at timestamp 15, the speed is −5 views per timestamp. The pattern analysis subsystem 15 may detect that the direction of navigation changes at timestamp 15 at again at timestamp 16. A consecutive sequence of changes of navigation directions may be considered a zigzag navigation pattern. Consequently, the pattern analysis subsystem 140 may detect a zigzag navigation pattern occurring at timestamps 15 and 16.

Having determined the navigation pattern, the pattern analysis subsystem 140 selects one of the plurality of system functions for execution by the function execution subsystem 160. For that purpose, the pattern analysis subsystem 140 may make use of mapping data 024 which is indicative of an association between the navigation pattern and the one of the plurality of system functions. As such, the pattern analysis subsystem 140 may be arranged for using mapping data 024 to select the one of the plurality of system functions 500 based on the navigation pattern. The mapping data 024 may be constituted by a look-up table, pre-defined rules or other types of data which link a particular navigation pattern to a particular system function. The mapping data 024 may be manually generated. Accordingly, the pattern analysis 140 may select a system function for execution. Here, the term 'selected for execution' refers to a selection by the system for the purpose of being executed. Consequently, the function execution subsystem 160 may directly execute the selected system function, i.e., without further interaction with the user, or rather only on confirmation by the user after first suggesting the execution of the system function to the user.

An example of the selecting of system functions based on the navigation pattern is the following. It is noted that although this and other examples are from a medical context, the present invention may equally applied in other contexts, i.e., is not limited to such medical context. In the example, the pattern analysis subsystem 140 is arranged for distinguishing between the user navigating continuously at a high navigation speed and the user navigating continuously at a low navigation speed. The former behavior is henceforth also referred to as rapid scrolling, whereas the latter is henceforth also referred to as slow scrolling. Rapid scrolling, which involves to the user viewing a large number of views in a short period, typically occurs when radiologists survey an image stack. Such surveys usually take place at the beginning of an image interpretation workflow, i.e., during a survey phase of the image interpretation workflow which typically takes place between the pre-reading phase and the interpretation phase. By detecting such rapid scrolling, the system 100 is enabled to suggest system functions related to the survey of the image to the user, such as image annotation functions. Rapid scrolling may also take place when radiologists exam spinal structures. For example, in case of CT chest abdomen and pelvis studies, radiologists may switch to the window level/width setting to the bone window and scroll rapidly through the views. When detecting such rapid scrolling, in combination with the window level/width settings, the system 100 can suggest system functions related to bone analysis.

The aforementioned slow scrolling, i.e., navigating continuously at a low navigation speed, mostly takes place when the radiologist is performing finding-specific analysis: viewing, measuring, and comparing. By detecting such slow scrolling, the system 100 can suggest system functions specific to finding-specific analysis, such as distance measurement tools. Moreover, in combination of anatomy information of the organs in the image and window level/width settings, certain imaging processing functions can be promoted, visualized, prioritized, or automatically executed by the system 100.

The determining of rapid scrolling and slow scrolling may be performed in various ways. For example, the pattern analysis subsystem 140 may determine the navigation speed during the navigation from time-stamped navigation commands 022. Accordingly, the pattern analysis subsystem 140 may distinguish between the rapid scrolling and the slow scrolling by comparing the navigation speed to one or more speed thresholds. Such speed thresholds may be preset or learned by the system, e.g., during a learning phase.

In addition to the navigation commands 022, the pattern analysis subsystem 140 may use further input to determine the navigation pattern. For example, in case of rapid scrolling and slow scrolling, it has been found that when the user uses a scroll wheel of the user input device 020 to navigate slowly through the image data 020, the user's finger may need to return to the anterior position of the scroll wheel to continue scrolling once it reaches the posterior position of the scroll wheel. The movement of the user's finger may be a rapid movement when the user is slowly scrolling. Moreover, the movement of the user's finger might be slow movement when the user is rapidly scrolling. This information may be measured and used by the system 100 to avoid false detection of the rapid or slow scrolling.

It is noted that, in general, the mapping data 024 may be constituted by a history of requests and associated navigation patterns of the user. Accordingly, the mapping data 024 may comprise or be indicative of one or more past requests of the user and navigation patterns as determined at a time of the past requests. For example, the mapping data 024 may indicate that, at a time of requesting an image measurement function, the user was deemed to use a stationary navigation pattern. Similarly, the mapping data 024 may indicate that, at a time of requesting an image analysis function, the user was deemed to use a zigzag navigation pattern. The mapping data 024 may also indicate that at a time when the user was deemed to use a continuous scrolling pattern, no system function was requested. Accordingly, when the current navigation pattern is deemed to be a zigzag navigation pattern, the pattern analysis subsystem 140 may use the mapping data 024 to determine that the user intends to request an image analysis function and thus select said function for execution.

The pattern analysis subsystem 140 may be arranged for applying machine learning to the history of requests and associated navigation patterns of the user for enabling selecting the one of the plurality of system functions 500 based on a presumed request of the user. Accordingly, the mapping data may be constituted by a look-up table, pre-defined rules or other types of data which were automatically generated using machine learning.

The pattern analysis subsystem 140 may also make use of other types of techniques to selects the one of the plurality of system functions 500 for execution based on the navigation pattern. For example, the pattern analysis 140 may make use of reasoning techniques as are known per se from the field of reasoning engines and inference engines.

Examples of system functions that may be selected by the pattern analysis subsystem 140 for execution include the following. The pattern analysis subsystem 140 may determine that the user focuses on a selected number of views, e.g., by determining a stationary navigation pattern. In response, the pattern analysis subsystem 140 may automatically select an image processing function, e.g., an organ segmentation function or a lesion detection function. In addition, the pattern analysis subsystem 140 may select system functions which perform one or more of the following actions:

1. A toolbox for image processing may be moved closer to the cursor. Accordingly, the user needs less movement of the cursor to access the toolbox.
2. A cursor model may be turned from a selection mode to the measuring mode. The measuring mode may be associated with a number of different image measurement functions, such as, e.g., a distance measurement, an angle measurement, a region of interest surface measurement, a freehand surface measurement, etc. The pattern analysis subsystem 140 may choose a preset of one of the image measurement function, a first one in a list, a last-one used, a most frequently-used one, etc.
3. The cursor model may be turned into an annotation model.
4. Image processing functions may be used to change the window level and width, zoom into a region of interest, etc.
5. A message may be generated prompting the user whether he/she desires to register the image data with other image data of a current study or of prior studies, apply lesion detection/segmentation algorithms, apply anatomy segmentation algorithms, generate an alternative view, register/link multiple image series, save the current image as key image, etc.
6. Another message may be generated prompting the user whether the system should search for similar studies in a database or look for further information, e.g., in medical encyclopedias or guideline databases.
7. Another message may be generated prompting the user whether he/she desires to include a report snippet in a report. An example of the report snipping may be the following: "In Series 1 Lungs, Slice 4-6: There is a . . . " with " . . . " constituting a placeholder in which a user such as a radiologist may provide his/her own observations.
8. A scrollbar-like navigational aid may be displayed which indicates the more-frequently-visited views of the image data. The user may click on the navigational aid to navigate directly to the more-frequently visited views. The user may also save the views as key images.

The pattern analysis subsystem 140 may also be arranged for obtaining contextual information of the study of the image data, and selecting the one of the plurality of system functions 500 further based on the contextual information. Referring back to FIG. 1, the pattern analysis subsystem 140 is shown to receive metadata 182 of the image data 042. The metadata 182 may enable the pattern analysis subsystem 140 to determine which content the image data 042 comprises, an image modality, a slice thickness, a number slices, etc. FIG. 1 further shows the system 100 comprising an image analysis subsystem 180 for analyzing a content of the image data 042. The image analysis subsystem 180 is shown to provide a result 184 of said analyzing to the pattern analysis subsystem 140 to provide contextual information of the study of the image data 042. The image analysis subsystem 180 may be arranged for segmenting an anatomical structure and/or lesion in medical image data 042. Although not shown in FIG. 1, the pattern analysis subsystem 140 may be arranged for obtaining other types of contextual information such as, e.g., workflow information indicating a current phase of the study and study information indicating a reason for the study.

An example of the use of such contextual information is the following. The study may be a CT chest and pelvis study. The system 100 may determine from DICOM headers of the image data 042 that the current modality is CT and the current body part is the abdomen of a patient. The image analysis subsystem 180 may segment the anatomical structures in the image data 042 so as to detect the lung in the image data 042. When the user is viewing the lung and when the navigation pattern has been determined to be a zigzag or stationary navigation pattern, the system 100 may automatically change the window level and width of the current view and detect lung nodules in the image data 042.

It is noted that, in general, the term view refers to a representation of at least a portion of the image data 042. The image data 042 may be 3D image data. The representation of the portion of the image data 042 may be in the form of a 2D image or a 3D image. The latter may be for display on a 3D display. Each view may be established by any suitable technique from the technical field of image data visualization, such as a multi-planar reformatting (MPR) technique or a maximum intensity projection (MIP) technique.

The user interface subsystem 120 may enable the user to simultaneously navigate in different views of the image data, e.g., in an axial, sagittal and coronal viewport. The pattern analysis subsystem 140 may be arranged for determining a navigation pattern for each viewport separately and subsequently combine them into a combined navigation pattern. Alternatively, the pattern analysis subsystem 140 may directly determine the combined navigation pattern. The combined navigation pattern may be used to select one of the plurality of system functions for execution by the function execution subsystem 160.

The display output processor 110 itself may generate the different views 400. Alternatively, the display output processor 110 may request the different views 400 from another subsystem or system. Moreover, the user interface subsystem 120 may, instead of being comprised of a user interface input 115 and a display output processor 110, take any other suitable form. For example, the user interface subsystem 120 may be arranged for instructing an external display output processor to display the different views 400.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling study of image data, comprising:
   a user interface subsystem comprising a user interface input connected to a user input device and a display output processor, said user interface subsystem configured to i) receive navigation commands from a user, and ii) display different views of the image data in response to the navigation commands for enabling the user to navigate through the image data; and
   a processor configured to:
      execute individual ones of a plurality of system functions to support the user in the study of the image data,
      obtain, from the user interface subsystem, data indicative of a display sequence of the different views during the navigating through the image data,
      analyze the data to determine a navigation pattern of the user, wherein the navigation pattern is one of the group of: a stationary navigation pattern, a continuous navigation pattern, and a zigzag navigation pattern, and
      based on the navigation pattern, select one of the plurality of system functions for execution by the function execution subsystem.

2. The system according to claim 1, wherein the pattern analysis subsystem is arranged for, after selecting the one of the plurality of system functions, i) instructing the function execution subsystem to execute said system function, or ii) instructing the user interface subsystem to visually indicate the system function to the user for enabling the user to request the execution of the system function.

3. The system according to claim 1, wherein the pattern analysis subsystem is arranged for using mapping data to select the one of the plurality of system functions based on the navigation pattern, the mapping data being indicative of an association between the navigation pattern and the one of the plurality of system functions.

4. The system according to claim 3, wherein the user interface subsystem is arranged for enabling the user to request execution of the individual ones of the plurality of system functions, and wherein the mapping data is constituted by a history of requests and associated navigation patterns of the user.

5. The system according to claim 4, wherein the pattern analysis subsystem is arranged for applying machine learning to the history of requests and associated navigation patterns of the user for enabling selecting the one of the plurality of system functions based on a presumed request of the user.

6. The system according to claim 1, wherein the pattern analysis subsystem is arranged for determining the navigation pattern by:
 based on the data determining a display parameter for each of the different views, each of said display parameters characterizing the display of a respective one of the different views during the navigation; and
 analyzing the display parameters to determine the navigation pattern.

7. The system according to claim 6, wherein the display parameter is one of the group of: a display duration, a display frequency, a navigation speed at a time of display, and a navigation direction at a time of display.

8. The system according to claim 1, wherein the continuous navigation pattern has a navigation speed below a speed threshold or a navigation speed above the speed threshold.

9. The system according to claim 1, wherein the pattern analysis subsystem is arranged for i) obtaining contextual information of the study of the image data, and ii) selecting the one of the plurality of system functions further based on the contextual information.

10. The system according to claim 9, wherein the pattern analysis subsystem is arranged for obtaining the contextual information from at least one of the group of: metadata of the image data, workflow information indicating a current phase of the study and study information indicating a reason for the study.

11. The system according to claim 9, further comprising an image analysis subsystem for analyzing a content of the image data for establishing the contextual information of the study of the image data.

12. The system according to claim 11, wherein the image data is medical image data, and wherein the image analysis subsystem is arranged for analyzing the content of the medical image data based on segmenting an anatomical structure and/or lesion in the medical image data.

13. A workstation or imaging system for enabling study of image data, the system comprising:
 a user interface input connected to a user input device for receiving navigation commands from a user;
 a display output processor for displaying different views of the image data in response to the navigation commands for enabling the user to navigate through the image data; and
 a processor configured to:
  execute individual ones of a plurality of system functions to support the user in the study of the image data,
  obtain data indicative of a display sequence of the different views during the navigating through the image data,
  analyze the data to determine a navigation pattern of the user, wherein the navigation pattern is one of the group of: a stationary navigation pattern, a continuous navigation pattern, and a zigzag navigation pattern, and
  based on the navigation pattern, select one of the plurality of system functions for execution by the function execution subsystem.

14. A method for controlling a computer for enabling study of image data, comprising:
 receiving, from a user interface input connected to a user input device, navigation commands from a user;
 displaying, via a display output processor, different views of the image data in response to the navigation commands for enabling the user to navigate through the image data; and
 executing, via a processor, individual ones of a plurality of system functions to support the user in the study of the image data;
the method further comprising:
 obtaining, via the processor, data indicative of a display sequence of the different views during the navigating through the image data;
 analyzing, via the processor, the data to determine a navigation pattern of the user, wherein the navigation pattern is one of the group of: a stationary navigation pattern, a continuous navigation pattern, and a zigzag navigation pattern;
 based on the navigation pattern, selecting, via the processor, one of the plurality of system functions for said executing.

15. A computer program product stored on a non-transitory computer readable medium comprising instructions for causing a processor system to perform the method according to claim 14.

* * * * *